(12) United States Patent
Knuebel et al.

(10) Patent No.: US 7,211,119 B2
(45) Date of Patent: May 1, 2007

(54) COUPLING COMPONENTS

(75) Inventors: George Knuebel, Duesseldorf (DE); Horst Hoeffkes, Duesseldorf (DE); Ralph Nemitz, Juechen (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 0 days.

(21) Appl. No.: 11/165,001

(22) Filed: Jun. 23, 2005

(65) Prior Publication Data

US 2006/0000032 A1 Jan. 5, 2006

Related U.S. Application Data

(63) Continuation of application No. PCT/EP03/014363, filed on Dec. 17, 2003.

(30) Foreign Application Priority Data

Dec. 23, 2002 (DE) ................................. 102 60 834

(51) Int. Cl.
*A61K 7/13* (2006.01)
(52) U.S. Cl. .................... 8/405; 8/406; 8/408; 8/411; 8/412; 8/421
(58) Field of Classification Search .................... 8/405, 8/406, 408, 411, 412, 421
See application file for complete search history.

(56) References Cited

U.S. PATENT DOCUMENTS

| | | | |
|---|---|---|---|
| RE30,199 E | 1/1980 | Rose et al. ................. 8/102 |
| 4,854,935 A | 8/1989 | Clausen et al. .............. 8/408 |
| 4,865,774 A | 9/1989 | Fabry et al. ................ 254/551 |
| 4,931,218 A | 6/1990 | Schenker et al. ........... 254/551 |
| 4,960,432 A | 10/1990 | Junino et al. ................ 8/411 |
| 5,061,289 A | 10/1991 | Clausen et al. .............. 8/417 |
| 5,294,726 A | 3/1994 | Behler et al. ............... 554/198 |
| 5,380,340 A | 1/1995 | Neunhoeffer et al. ......... 8/409 |
| 5,534,267 A | 7/1996 | Neunhoeffer et al. ......... 8/209 |
| 5,663,366 A | 9/1997 | Neunhoeffer et al. .... 548/137.4 |
| 5,766,576 A | 6/1998 | Löwe et al. ................ 284/554 |
| 6,024,769 A * | 2/2000 | Cotteret ...................... 8/411 |
| 6,099,592 A | 8/2000 | Vidal et al. ................ 424/62 |
| 6,284,003 B1 | 9/2001 | Rose et al. .................. 8/417 |

FOREIGN PATENT DOCUMENTS

| | | |
|---|---|---|
| CA | 2 288 253 | 1/2001 |
| DE | 23 59 399 A1 | 6/1975 |
| DE | 37 23 354 A1 | 1/1989 |
| DE | 37 25 030 A1 | 2/1989 |
| DE | 3 843 892 A1 | 6/1990 |
| DE | 39 26 344 A1 | 2/1991 |
| DE | 4 133 957 A1 | 4/1993 |
| DE | 195 43 988 A1 | 5/1997 |
| EP | 0 294 669 A1 | 12/1988 |
| EP | 0 740 931 B1 | 8/1997 |
| EP | 0 998 908 A2 | 10/1999 |
| GB | 1 026 978 | 4/1966 |
| GB | 1 153 196 | 5/1969 |
| JP | 02-019576 A2 | 1/1990 |
| WO | WO 88/00042 A1 | 1/1988 |
| WO | WO 93/10744 A2 | 6/1993 |
| WO | WO 94/08969 A1 | 4/1994 |
| WO | WO 94/08970 A1 | 4/1994 |
| WO | WO 96/15765 A1 | 5/1996 |

OTHER PUBLICATIONS

STIC Search Report Jan. 23, 2006.*
C. Zviak, "Nonoxidation Coloring", The Science of Hair Care, Chapter 7, pp. 248-250, published in vol. 7 of Dermatology, Marcel Dekker Inc. NY/Baste (1986).
C. Zviak, "Oxidation Colouring", The Science of Hair Care, Chapter 8, pp. 263-286, published in vol. 7 of Dermatology, Marcel Dekker Inc. NY/Basel (1986).
"Dermatology", Verlag Marcel Dekker Inc., New Yor, Basel (1986).
EU Inventory of Cosmetic Ingredients, Colipa, Mar. 1996 on diskette.
K. Schrader, Grundlagen und Rezepturen der Kosmetika, 2$^{nd}$ Edition, Huthig Buch Verlag, Heidelberg (1989).
Taschenlexikon der Farben, A Kornerup, 3$^{rd}$ Edition, Muster-Schmidt Verlag, Zurich Gottingen (1981).

* cited by examiner

*Primary Examiner*—Eisa Elhilo
(74) *Attorney, Agent, or Firm*—John S. Child, Jr.

(57) ABSTRACT

Keratin fibers are colored by an agent comprising a coupler which is a m-phenylenediamine derivative of the formula (I)

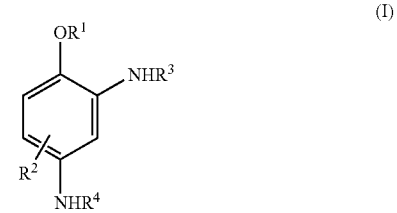

wherein $R^1$ is a $C_1$–$C_4$ alkyl group or a $C_1$–$C_4$ monohydroxyalkyl group; $R^2$ is a methyl or an ethyl group; each of $R^3$ and $R^4$ is independently a branched or unbranched $C_2$–$C_6$ hydroxyalkyl group; and a cosmetically acceptable carrier. These couplers exhibit improved toxicological and dermatological properties and permit hair colorations in a broad color spectrum with good fastness properties.

20 Claims, No Drawings

COUPLING COMPONENTS

CROSS REFERENCE TO RELATED APPLICATIONS

This application is a continuation under 35 U.S.C. § 365(c) and 35 U.S.C. § 120 of international application PCT/EP2003/014363, filed on Dec. 17, 2003. This application also claims priority under 35 U.S.C. § 119 of DE 102 60 834.2, filed Dec. 23, 2002 each of which is incorporated herein by reference in its entirety.

BACKGROUND OF THE INVENTION

The present invention relates to agents for coloring keratin fibers which comprise special m-phenylenediamine derivatives, to a method of coloring hair using these agents, and to some of these m-phenylenediamine derivatives themselves and intermediates which are formed during the preparation of these compounds.

For the coloring of keratin fibers, in particular human hair, so-called oxidation colorants play a preferred role due to their intense colors and good fastness properties. Such colorants comprise oxidation dye precursors, so-called developer components and coupler components. The developer components form the actual dyes under the influence of oxidizing agents or of atmospheric oxygen with one another or with coupling with one or more coupler components.

The developer components used are usually primary aromatic amines with a further free or substituted hydroxyl or amino group located in the para or ortho position, diaminopyridine derivatives, heterocyclic hydrazones, 4-aminopyrazolone derivatives, and 2,4,5,6-tetraminopyrimidine and derivatives thereof.

Examples of developer components include, but are not limited to, p-phenylenediamine, p-tolylenediamine, 2,4,5,6-tetraminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxamido-4-aminpyrazol-5-one, 4-amino-3-methylphenol, 2-aminomethyl-4-aminophenol, 2-hydroxy-4,5,6-triaminopyrimidine, 2,4-dihydroxy-5,6-diaminopyrimidine, 2,5,6-triamino-4-hydroxypyrimidine and 1,3-N,N'-bis(2-hydroxyethyl)-N,N'-bis(4-aminophenyl)diaminopropan-2-ol.

Typical coupler components include, but are not limited to, m-phenylenediamine derivatives, naphthols, resorcinol and resorcinol derivatives, pyrazolones and m-aminophenols. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazol-5-one, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol, 5-methylresorcinol and 2-methyl-4-chloro-5-aminophenol.

Good oxidation dye precursors should firstly satisfy the following prerequisites: during oxidative coupling, they must form the desired shades in an adequate intensity and fastness. They must also have a good ability to attach to the fibers and particularly for human hair there should be no notable differences between stressed and freshly grown hair (equalizing ability). They should be resistant to light, heat, perspiration, rubbing and the effect of chemical reducing agents, e.g. permanent waving liquids. Finally, if used as hair colorants, they should not color the scalp excessively, and in particular they should be acceptable from a toxico-logical and dermatological point of view. In addition, it should be possible to readily remove the coloration achieved from the hair again by bleaching if it does not correspond to the individual wishes of the individual person and is to be reversed.

Using a developer component or a special coupler/developer combination on its own it is generally not possible to obtain a shade which looks natural on the hair. In practice, therefore, use is usually made of combinations of different developer and/or coupler components. There is therefore a continuing need for novel improved dye components which are also unproblematic from a toxicological and dermatological point of view.

It was therefore one object of the present invention to develop novel coupler components which satisfy the requirements placed on oxidation dye precursors, especially with regard to the toxicological and dermatological properties, and permit colorations in a broad color spectrum with good fastness properties.

SUMMARY OF THE INVENTION

Surprisingly, it has now been found that special m-phenylenediamine derivatives satisfy the requirements placed on coupler components to a high degree. The coupler components according to the invention permit, particularly with p-tolylenediamine, 1-(2-hydroxyethyl)-2,5-diaminobenzene, 2,4,5,6-tetraminopyrimidine and bis(2-hydroxy-5-aminophenyl)methane, colorations with high color intensities and good to very good fastness properties in the red and violet range.

DETAILED DESCRIPTION OF THE INVENTION

The present invention therefore firstly provides agents for coloring keratin fibers, in particular human hair, comprising, in a cosmetically acceptable carrier, as coupler component at least one m-phenylenediamine derivative of the formula (I)

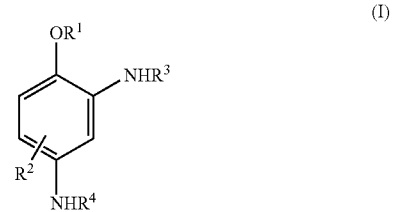

where $R^1$ is a $C_1$- to $C_4$-alkyl group or a $C_1$- to $C_4$-monohydroxyalkyl group,
$R^2$ is a methyl or an ethyl group, and
$R^3$ and $R^4$, independently of one another, are a branched or unbranched $C_2$- to $C_6$-hydroxyalkyl group.

According to the invention, keratin fibers are understood here as meaning furs, wool, feathers and in particular human hair. Although the oxidation colorants according to the invention are primarily suitable for coloring keratin fibers, there is in principle nothing to prevent use also in other fields, in particular in color photography.

Since the m-phenylenediamine derivatives according to the invention are amino compounds, the known acid addition salts can be prepared from these in the usual way. All of the statements in this specification and accordingly the claimed scope of protection therefore refer both to the compounds present in free base form and also to their water-soluble, physiologically compatible salts. Examples of such salts are the hydrochlorides, the hydrobromides, the sulfates, the phosphates, the acetates, the propionates, the citrates and the lactates. The hydrochlorides and the sulfates are particularly preferred here.

Examples of the $C_1$- to $C_6$-alkyl groups specified as substituents in the compounds according to the invention are the groups methyl, ethyl, propyl, isopropyl, butyl, pentyl and hexyl. Ethyl and methyl are preferred alkyl groups. Preferred $C_1$- to $C_6$-mono-hydroxyalkyl groups which may be mentioned are a hydroxymethyl group, a 2-hydroxyethyl group, a 3-hydroxypropyl group or a 4-hydroxybutyl group. A 2-hydroxyethyl group is particularly preferred.

The m-phenylenediamine derivatives of the formula (I) can be prepared using conventional organic methods. By way of example, reference may be made at this point to the experimental procedures within the scope of the working examples.

A number of structurally related m-phenylenediamine derivatives are already known as coupler components from the prior art. Thus, for example, international laid-open specification WO-A1-88/00 042 proposes 5-alkoxy-2,4-diamino-1-alkylbenzenes as coupler components which permit intense blue colorations without a red or green tinge using the developer component p-tolylenediamine. These coupler components differ from the compounds of the formula (I) now being proposed in that the amino groups are unsubstituted. Surprisingly, the amino-group-substituted compounds now claimed permit intense red to red-violet colorations with developer components such as, for example, p-tolylenediamine. Moreover, the international laid-open specification WO-A2-93/10 744 discloses a method of coloring hair in an acidic medium (pH<7) in which structurally related m-phenylenediamine derivatives are used. The compound 2,4-di(β-hydroxyethylamino-1-methoxybenzene is specifically described therein. The compounds now claimed differ from this compound in that they have a further alkyl group on the aromatic ring. This specification reveals no indications of the compounds now claimed and their excellent coloring properties and the brilliant nuances which can be achieved in the red range either.

According to the invention, the m-phenylenediamine derivatives of the formula (I) in which the substituents $R^3$ and $R^4$ are identical may be preferred. In each case, the substituents $R^3$ and $R^4$ are particularly preferably a 2-hydroxyethyl group or a 3-hydroxypropyl group. A 2-hydroxyethyl group is very particularly preferred.

In addition, according to the invention, the m-phenylenediamine derivatives of the formula (I) in which the substituent $R^1$ is a $C_1$- to $C_4$-alkyl group may be preferred. Particular preference is given to the compounds of the formula (I) in which $R^1$ is a methyl group.

In addition, according to the invention, the m-phenylenediamine derivatives of the formula (I) in which $R^2$ is a methyl group may be preferred.

The following compounds are encompassed within the scope of the present invention:

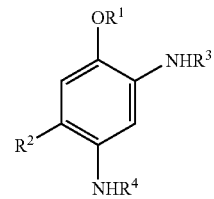

(Ia)

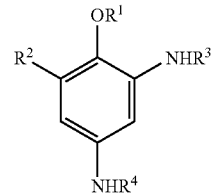

(Ib)

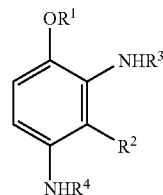

(Ic)

Within the scope of this embodiment, particular preference is given to the compounds of the formulae (Ib) and (Ic). Particular preference is given to the compounds 2,4-bis[(2-hydroxyethyl)amino]-6-methylanisole and 2,4-bis[(3-hydroxypropyl)amino]-6-methylanisole. 2,4-Bis[(2-hydroxyethyl)amino]-6-methylanisole is a compound which is very particularly preferred according to the invention.

Besides the m-phenylenediamine derivatives of the formula (I), the colorants according to the invention can also comprise at least one developer component.

The developer components used are usually primary aromatic amines with a further free or substituted hydroxyl or amino group located in the para or ortho position, diaminopyridine derivatives, heterocyclic hydrazones, 4-aminopyrazole derivatives and 2,4,5,6-tetraminopyrimidine and derivatives thereof.

According to the invention, it may be preferred to use as developer component a p-phenylenediamine derivative or one of its physiologically compatible salts. Particular preference is given to p-phenylenediamine derivatives of the formula (E1)

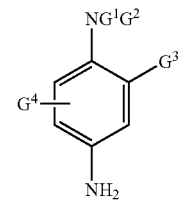

(E1)

where
  $G^1$ is a hydrogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a 4'-aminophenyl radical or a ($C_1$- to C₄)-alkyl radical which is substituted by a nitrogen-containing group, a phenyl radical or a 4'-aminophenyl radical;

G² is a hydrogen atom, a ($C_1$- to $C_4$)-alkyl radical, a ($C_1$- to $C_4$)-monohydroxyalkyl radical, a $C_2$- to $C_4$-polyhydroxyalkyl radical, a ($C_1$- to $C_4$)-alkoxy-($C_1$- to $C_4$)-alkyl radical or a $C_1$- to $C_4$-alkyl radical which is substituted by a nitrogen-containing group;

G³ is a hydrogen atom, a halogen atom, such as a chlorine, bromine, iodine or fluorine atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-hydroxyalkoxy radical, a $C_1$- to $C_4$-acetylaminoalkoxy radical, a $C_1$- to $C_4$-mesylaminoalkoxy radical or a $C_1$- to $C_4$-carbamoylaminoalkoxy radical;

G⁴ is a hydrogen atom, a halogen atom or a $C_1$- to $C_4$-alkyl radical or if G³ and G⁴ are in the ortho position relative to one another, they can together form a bridging α,ω-alkylenedioxo group, such as, for example, an ethylenedioxy group.

Examples of the $C_1$- to $C_4$-alkyl radicals specified as substituents in the compounds according to the invention are the groups methyl, ethyl, propyl, isopropyl and butyl. Ethyl and methyl are preferred alkyl radicals. $C_1$- to $C_4$-alkoxy radicals preferred according to the invention are, for example, a methoxy or an ethoxy group. In addition, preferred examples of a $C_1$- to $C_4$-hydroxyalkyl group which may be mentioned are a hydroxymethyl group, a 2-hydroxyethyl group, a 3-hydroxypropyl group or a 4-hydroxybutyl group. A 2-hydroxyethyl group is particularly preferred. A particularly preferred $C_2$- to $C_4$-polyhydroxyalkyl group is the 1,2-dihydroxyethyl group. Examples of halogen atoms according to the invention are F, Cl or Br atoms; Cl atoms are very particularly preferred. The further terms used are derived according to the invention from the definitions given here. Examples of nitrogen-containing groups of the formula (E1) are in particular the amino groups, $C_1$- to $C_4$-monoalkylamino groups, $C_1$- to $C_4$-dialkylamino groups, $C_1$- to $C_4$-trialkylammonium groups, $C_1$- to $C_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and their physiologically compatible salts.

p-Phenylenediamine derivatives of the formula (E1) which are very particularly preferred according to the invention are p-phenylenediamine, p-tolylenediamine, 2-(β-hydroxyethyl)-p-phenylenediamine, 2-(α,β-dihydroxyethyl)-p-phenylenediamine and N,N-bis(β-hydroxyethyl)-p-phenylenediamine.

According to the invention, it may be further preferred to use compounds which contain at least two aromatic nuclei which are substituted by amino and/or hydroxyl groups as developer component.

Of the binuclear developer components which can be used in the coloring compositions according to the invention, specific mention may be made of the compounds which correspond to the following formula (E2), and their physiologically compatible salts:

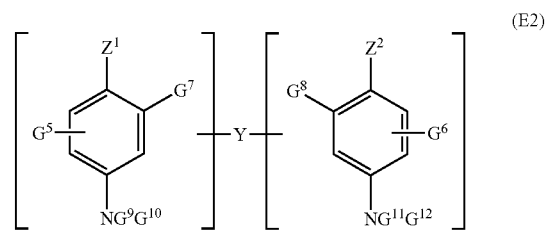

(E2)

where:

Z¹ and Z², independently of one another, are a hydroxyl or NH₂ radical which is optionally substituted by a $C_1$- to $C_4$-alkyl radical, by a $C_1$- to $C_4$-hydroxyalkyl radical and/or by a bridge Y or which is optionally part of a bridging ring system, the bridge Y is an alkylene group having 1 to 14 carbon atoms, such as, for example, a linear or branched alkylene chain or an alkylene ring which may be interrupted or terminated by one or more nitrogen-containing groups and/or one or more heteroatoms such as oxygen, sulfur or nitrogen atoms and may possibly be substituted by one or more hydroxyl or $C_1$- to $C_8$-alkoxy radicals, or a direct bond, G⁵ and G⁶, independently of one another, are a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-aminoalkyl radical or a direct linkage to the bridge Y, G⁷, G⁸, G⁹, G¹⁰, G¹¹ and G¹², independently of one another, are a hydrogen atom, a direct bond to the bridge Y or a $C_1$- to $C_4$-alkyl radical, with the provisos that the compounds of the formula (E2) contain only one bridge Y per molecule and the compounds of the formula (E2) contain at least one amino group which carries at least one hydrogen atom.

According to the invention, the substituents used in formula (E2) are defined analogously to the above statements.

Preferred binuclear developer components of the formula (E2) are in particular: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'diethyl-N,N'-bis(4'-amino-3'-methylphenyl) ethylenediamine, bis(2-hydroxy-5-aminophenol)-methane, 1,3-bis(2,5-diaminophenoxy)propan-2-ol, N,N'-bis(4'-diaminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Very particularly preferred binuclear developer components of the formula (E2) are N,N'-bis(β-hydroxyethyl)-N,N'-bis(4'-aminophenyl)-1,3-diaminopropan-2-ol, bis(2-hydroxy-5-aminophenyl)methane, 1,3-bis(2,5-diaminophenoxy)propan-2-ol, N,N'-bis(4'-aminophenyl)-1,4-diazacycloheptane and 1,10-bis(2',5'-diaminophenyl)-1,4,7,10-tetraoxadecane or one of their physiologically compatible salts.

Bis(2-hydroxy-5-aminophenyl)methane is a very particularly preferred binuclear developer component of the formula (E2).

In addition, it may be preferred according to the invention to use a p-aminophenol derivative or one of its physiologically compatible salts as developer component. Particular preference is given to p-aminophenol derivatives of the formula (E3)

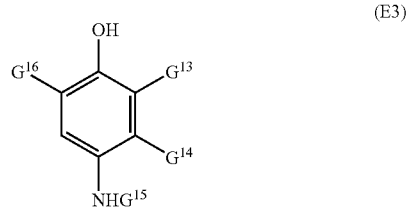

where
G$^{13}$ is a hydrogen atom, a halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a $C_1$- to $C_4$-aminoalkyl radical, a hydroxy($C_1$- to $C_4$)alkylamino radical, a $C_1$- to $C_4$-hydroxyalkoxy radical, a $C_1$- to $C_4$-hydroxyalkyl($C_1$- to $C_4$)aminoalkyl radical or a (di-$C_1$- to $C_4$-alkylamino) ($C_1$- to $C_4$)alkyl radical, and G$^{14}$ is a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)alkyl radical, a $C_1$- to $C_4$-aminoalkyl radical or a $C_1$- to $C_4$-cyanoalkyl radical, G$^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and G$^{16}$ is hydrogen or a halogen atom.

According to the invention, the substituents used in formula (E3) are defined analogously to the above statements.

Preferred p-aminophenols of the formula (E3) are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be chosen from o-aminophenol and its derivatives, such as, for example, 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazole-pyrimidine derivatives and their physiologically compatible salts.

Preferred pyridine derivatives are in particular the compounds which are described in the patents GB 1 026 978 and GB 1 153 196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are in particular the compounds which are described in the German patent DE 2 359 399, the Japanese laid-open specification JP 02019576 A2 or in the laid-open specification WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are in particular the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, 3,4,5-triaminopyrazole, 1-methyl-3,4,5-triaminopyrazole, 3,5-diamino-1-methyl-4-methylaminepyrazole and 3,5-diamino-4-(β-hydroxyethyl)amino-1-methylpyrazole.

Preferred pyrazolepyrimidine derivatives are in particular the derivatives of pyrazole[1,5-a]pyrimidine of the following formula (E4) and tautomeric forms thereof if there is a tautomeric equilibrium:

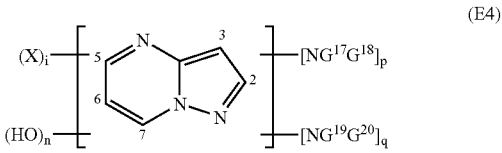

where:
G$^{17}$, G$^{18}$, G$^{19}$ and G$^{20}$, independently of one another, are a hydrogen atom, a $C_1$- to $C_4$-alkyl radical, an aryl radical, a $C_1$- to $C_4$-hydroxyalkyl radical, a $C_2$- to $C_4$-polyhydroxyalkyl radical, a ($C_1$- to $C_4$)-alkoxy($C_1$- to $C_4$)alkyl radical, a $C_1$- to $C_4$-aminoalkyl radical, which may optionally be protected by an acetylureido or a sulfonyl radical, a ($C_1$- to $C_4$)alkylamino($C_1$- to $C_4$)alkyl radical, a di[($C_1$- to $C_4$)alkyl]($C_1$- to $C_4$)aminoalkyl radical, where the dialkyl radicals optionally form a carbocycle or a heterocycle with 5 or 6 chain members, a $C_1$- to $C_4$-hydroxyalkyl or a di($C_1$- to $C_4$)[hydroxyalkyl]($C_1$- to $C_4$)aminoalkyl radical, the X radicals, independently of one another, are a hydrogen atom, a $C_1$- to $C_4$-alkyl radical, an aryl radical, a $C_1$- to $C_4$-hydroxyalkyl radical, a $C_2$- to $C_4$-polyhydroxyalkyl radical, a $C_1$- to $C_4$-aminoalkyl radical, a ($C_1$- to $C_4$)alkylamino($C_1$- to $C_4$)alkyl radical, a di[($C_1$- to $C_4$)alkyl]($C_1$- to $C_4$)aminoalkyl radical, where the dialkyl radicals optionally form a carbocycle or a heterocycle having 5 or 6 -chain members, a $C_1$- to $C_4$-hydroxyalkyl or a di($C_1$- to $C_4$-hydroxyalkyl)aminoalkyl radical, an amino radical, a $C_1$- to $C_4$-alkyl or di($C_1$- to $C_4$-hydroxyalkyl)amino radical, a halogen atom, a carboxylic acid group or a sulfonic acid group, i has the value 0, 1, 2 or 3,
p has the value 0 or 1,
q has the value 0 or 1 and
n has the value 0 or 1, with the proviso that
the sum of p+q does not equal 0,
if p+q is 2, n has the value 0, and the groups $NG^{17}G^{18}$ and $NG^{19}G^{20}$ occupy positions (2,3); (5,6); (6,7); (3,5) or (3,7);
if p+q is 1, n has the value 1, and the groups $NG^{17}G^{18}$ (or $NG^{19}G^{20}$) and the group OH occupy positions (2,3); (5,6); (6,7); (3,5) or (3,7).

According to the invention, the substituents used in formula (E4) are defined analogously to the above statements.

If the pyrazole[1,5-a]pyrimidine of the above formula (E4) contains a hydroxyl group on one of positions 2, 5 or 7 of the ring system, there is a tautomeric equilibrium, which is represented, for example, in the following scheme:

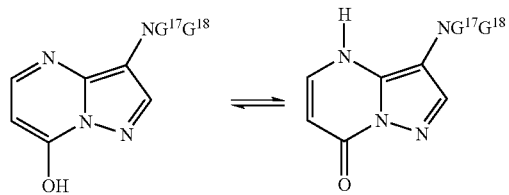

Of the pyrazole[1,5-a]pyrimidines of the above formula (E4), particular mention may be made of:
pyrazole[1,5-a]pyrimidine-3,7-diamine;
2,5-dimethylpyrazole[1,5-a]pyrimidine-3,7-diamine;
pyrazole[1,5-a]pyrimidine-3,5-diamine;
2,7-dimethylpyrazole[1,5-a]pyrimidine-3,5-diamine;
3-aminopyrazole[1,5-a]pyrimidin-7-ol;
3-aminopyrazole[1,5-a]pyrimidin-5-ol;
2-(3-aminopyrazole[1,5-a]pyrimidin-7-ylamino)-ethanol;
2-(7-aminopyrazole[1,5-a]pyrimidin-3-ylamino)-ethanol;
2-[(3-aminopyrazole[1,5-a]pyrimidin-7-yl)(2-hydroxyethyl)amino]ethanol;
2-[(7-aminopyrazole[1,5-a]pyrimidin-3-yl)(2-hydroxyethyl)amino]ethanol;
5,6-dimethylpyrazole[1,5-a]pyrimidine-3,7-diamine;
2,6-dimethylpyrazole[1,5-a]pyrimidine-3,7-diamine;
3-amino-7-dimethylamino-2,5-dimethylpyrazole[1,5-a]pyrimidine;

and their physiologically compatible salts and their tautomeric forms if a tautomeric equilibrium is present.

As described in the literature, the pyrazole[1,5-a]pyrimidines of the above formula (E4) can be prepared by cyclization starting from an aminopyrazole or from hydrazine.

In a further preferred embodiment, the colorants according to the invention comprise at least one further coupler component.

The coupler components usually used are m-phenylenediamine derivatives, naphthols, resorcinol and resorcinol derivatives, pyrazolones and m-aminophenol derivatives. Suitable coupler substances are in particular 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazol-5-one, 2,4-dichloro-3-aminophenol, 1,3-bis(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Coupler components preferred according to the invention are m-aminophenol and derivatives thereof, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2',4'-diaminophenoxy)propane, 1-methoxy-2-amino-4-(2'-hydroxyethylamino)benzene, 1,3-bis(2',4'-diaminophenol)propane, 2,6-bis(2'-hydroxyethylamino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- and trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or methylenedioxybenzene derivatives, such as, for example, 1-hydroxy-3,4-methylenedioxybenzene, 1-amino-3,4-methylenedioxybenzene and 1-(2'-hydroxyethyl)amino-3,4-methylenedioxybenzene.

Coupler components particularly preferred according to the invention are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

The following coupler/developer combinations have proven particularly suitable according to the invention:
2,4-bis[(2-hydroxyethyl)amino]-6-methylanisole/p-tolylenediamine,
2,4-bis[(2-hydroxyethyl)amino]-6-methylanisole/1-(2-hydroxyethyl)-2,5-diaminobenzene,
2,4-bis[(2-hydroxyethyl)amino]-6-methylanisole/bis(2-hydroxy-5-aminophenol)methane and
2,4-bis[(2-hydroxyethyl)amino]-6-methylanisole/2,4,5,6-tetraminopyrimidine.

The hair colorants according to the invention comprise both the developer components and also the coupler components preferably in an amount of from 0.005 to 20% by weight, preferably 0.1 to 5% by weight, in each case based on the total oxidation colorant. Here, developer components and coupler components are generally used in approximately molar amounts relative to one another. Even though the molar use has proven expedient, a certain excess of individual oxidation dye precursors is not disadvantageous, meaning that developer components and coupler components may be present in a mole ratio of from 1:0.5 to 1:3, in particular 1:1 to 1:2.

In a further embodiment of the present invention, the colorants can comprise at least one precursor of a nature-analogous dye. The precursors of nature-analogous dyes used are preferably those indoles and indolines which have at least one hydroxyl or amino group, preferably as substituent on the six-membered ring. These groups can carry further substituents, e.g. in the form of an etherification or esterification of the hydroxyl group or an alkylation of the amino group. In a second preferred embodiment, the colorants comprise at least one indole and/or indoline derivative.

Particularly highly suitable precursors of nature-analogous hair dyes are derivatives of 5,6-dihydroxyindoline of the formula (IIa),

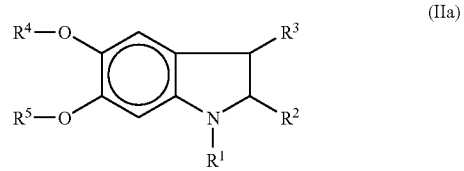

in which, independently of one another, $R^1$ is hydrogen, a $C_1$–$C_4$-alkyl group or a $C_1$–$C_4$-hydroxyalkyl group, $R^2$ is hydrogen or a —COOH group, where the —COOH group may also be in the form of a salt with a physiologically compatible cation, $R^3$ is hydrogen or a $C_1$–$C_4$-alkyl group, $R^4$ is hydrogen, a $C_1$–$C_4$-alkyl group or a group —CO— $R^6$, in which $R^6$ is a $C_1$–$C_4$-alkyl group, and $R^5$ is one of the groups specified under $R^4$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis should be placed on N-methyl-5,6-dihydroxyindoline, N-ethyl-5,6-dihydroxyindoline, N-propyl-5,6-dihydroxyindoline, N-butyl-5,6-dihydroxyindoline and in particular 5,6-dihydroxyindoline.

Of excellent suitability as precursors of nature-analogous hair dyes are also derivatives of 5,6-dihydroxyindole of the formula (IIb),

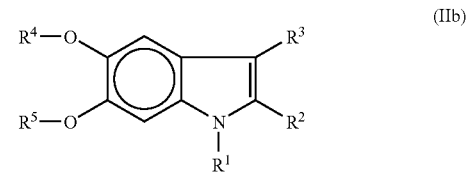

in which, independently of one another, $R^1$ is hydrogen, a $C_1$–$C_4$-alkyl group or a $C_1$–$C_4$-hydroxyalkyl group, $R^2$ is hydrogen or a —COOH group, where the —COOH group may also be in the form of a salt with a physiologically compatible cation, $R^3$ is hydrogen or a $C_1$–$C_4$-alkyl group, $R^4$ is hydrogen, a $C_1$–$C_4$-alkyl group or a group —CO— $R^6$, in which $R^6$ is a $C_1$–$C_4$-alkyl group, and $R^5$ is one of the groups specified under $R^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is placed on N-methyl-5,6-dihydroxyindole, N-ethyl-5,6-dihydroxyindole, N-propyl-5,6-dihydroxyindole, N-butyl-5,6-dihydroxyindole and in particular 5,6-dihydroxyindole.

The indoline and indole derivatives can be used in the colorants according to the invention either in the form of free bases or in the form of their physiologically compatible salts with inorganic or organic acids, e.g. the hydrochlorides, the sulfates and hydrobromides. The indole or indoline derivatives are usually present in these in amounts of 0.05–10% by weight, preferably 0.2–5% by weight.

In a further embodiment, it may be preferred according to the invention to use the indoline or indole derivative in colorants in combination with at least one amino acid or an oligopeptide. The amino acid is advantageously an α-amino acid; very particularly preferred α-amino acids are arginine, ornithine, lysine, serine and histidine, in particular arginine.

In a further preferred embodiment of the present invention, besides the m-phenylenediamine derivatives of the formula (I) according to the invention, the colorants according to the invention can comprise one or more direct dyes for the nuancing. Direct dyes are usually nitrophenylenediamines, nitroaminophenols, azo dyes, anthraquinones or indophenols. Preferred direct dyes are the compounds known under the international names and trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, and 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, the agents according to the invention comprise a cationic direct dye. Particular preference is given here to (a) cationic triphenylmethane dyes, such as, for example, Basic Blue 7, Basic Blue 26, Basic Violet 2 and Basic Violet 14, (b) aromatic systems which are substituted with a quaternary nitrogen group, such as, for example, Basic Yellow 57, Basic Red 76, Basic Blue 99, Basic Brown 16 and Basic Brown 17, and (c) direct dyes which contain a heterocycle which has at least one quaternary nitrogen atom, as are specified, for example, in EP-A2-998 908, which is hereby incorporated explicitly by reference, in claims 6 to 11.

Preferred cationic direct dyes of group (c) are in particular the following compounds:

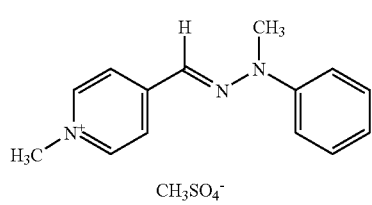
(DZ1)

-continued

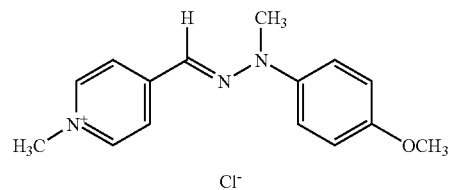
(DZ2)

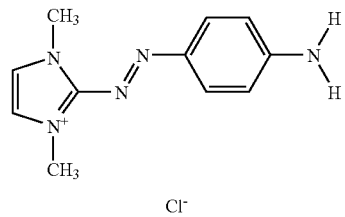
(DZ3)

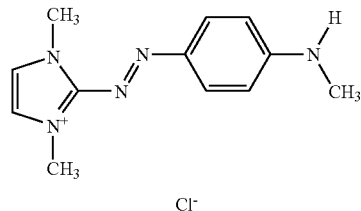
(DZ4)

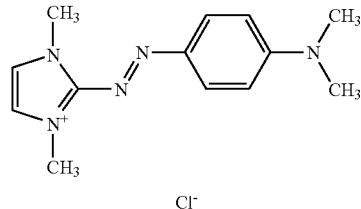
(DZ5)

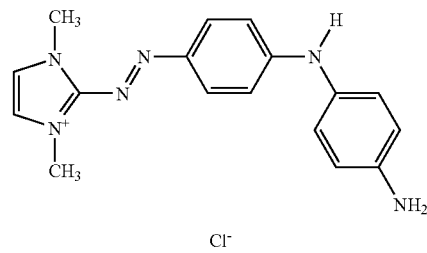
(DZ6)

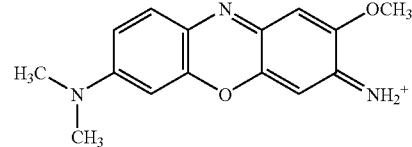
(DZ7)

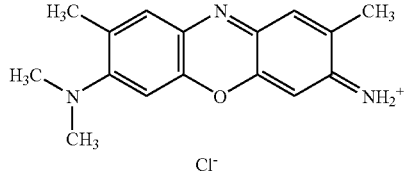
(DZ8)

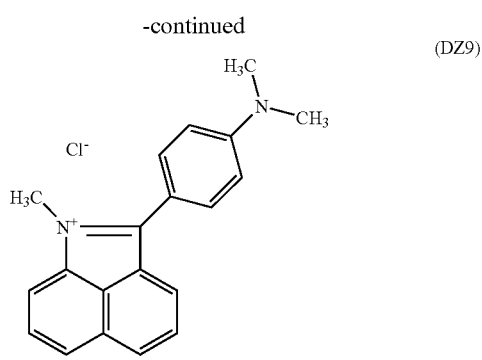

(DZ9)

The compounds of the formulae (DZ1), (DZ3) and (DZ5), which are also known under the names Basic Yellow 87, Basic Orange 31 and Basic Red 51, are very particularly preferred cationic direct dyes of group (c).

The cationic direct dyes which are sold under the trade name Arianor® are likewise very particularly preferred cationic direct dyes according to the invention.

According to this embodiment, the agents according to the invention comprise the direct dyes preferably in an amount of from 0.01 to 20% by weight, based on the total colorant.

In addition, the preparations according to the invention can also comprise dyes which occur in nature, as are present, for example, in henna red, henna neutral, henna black, camomile blossom, sandalwood, black tea, buckthorn bark, sage, logwood, madder root, catechu, sedre and alkanna root.

It is not necessary for the oxidation dye precursors or the direct dyes to each constitute uniform products. Rather, it is possible that, as a result of the preparation processes for the individual dyes, further components are present in minor amounts in the hair colorants according to the invention provided these do not adversely affect the dyeing result, or have to be excluded for other reasons, e.g. toxicological reasons.

With regard to the dyes which can be used in the hair colorants and tints according to the invention, reference is also made expressly to the monograph by Ch. Zviak, The Science of Hair Care, chapter 7 (pages 248–250; direct dyes), and chapter 8, pages 264–267; oxidation dye precursors), published as volume 7 of the "Dermatology" series (editors: Ch. Culnan and H. Maibach), Verlag Marcel Dekker Inc., New York, Basle, 1986, and the "European Inventory of Cosmetic Raw Materials", published by the European Commission, available in diskette format from the Bundesverband Deutscher Industrie—und Handelsunternehmen für Arzneimittel, Reformwaren und Körperpflegemittel e.V., Mannheim.

In addition, the colorants according to the invention can also comprise all active ingredients, additives and auxiliaries known for such preparations. In many cases, the colorants comprise at least one surfactant, with both anionic and also zwitterionic, ampholytic, nonionic and cationic surfactants being suitable in principle. In many cases, however, it has proven advantageous to choose the surfactants from anionic, zwitterionic or nonionic surfactants.

Suitable anionic surfactants in preparations according to the invention are all anionic surface-active substances suitable for use on the human body. These are characterized by a solubilizing, anionic group, such as, for example, a carboxylate, sulfate, sulfonate or phosphate group, and a lipophilic alkyl group having about 10 to 22 carbon atoms. In addition, glycol or polyglycol ether groups, ester, ether and amide groups, and hydroxyl groups may be present in the molecule. Examples of suitable anionic surfactants are, in each case in the form of the sodium, potassium and ammonium salts, and also the mono-, di- and trialkanolammonium salts having 2 or 3 carbon atoms in the alkanol group, linear fatty acids having 10 to 22 carbon atoms (soaps), ethercarboxylic acids of the formula R—O—($CH_2$—$CH_2O$)$_x$—$CH_2$—COOH, in which R is a linear alkyl group having 10 to 22 carbon atoms and x=0 or 1 to 16, acyl sarcosides having 10 to 18 carbon atoms in the acyl group, acyl taurides having 10 to 18 carbon atoms in the acyl group, acyl isethionates having 10 to 18 carbon atoms in the acyl group, sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups, linear alkanesulfonates having 12 to 18 carbon atoms, linear alpha-olefinsulfonates having 12 to 18 carbon atoms, alpha-sulfo fatty acid methyl esters of fatty acids having 12 to 18 carbon atoms, alkyl sulfates and alkyl polyglycol ether sulfates of the formula R—O($CH_2$—$CH_2O$)$_x$—$SO_3H$, in which R is a preferably linear alkyl group having 10 to 18 carbon atoms and x=0 or 1 to 12, mixtures of surface-active hydroxysulfonates according to DE-A-37 25 030, sulfated hydroxyalkylpolyethylene and/or hydroxyalkylenepropylene glycol ethers as in DE-A-37 23 354, sulfonates of unsaturated fatty acids having 12 to 24 carbon atoms and 1 to 6 double bonds as in DE-A-39 26 344, esters of tartaric acid and citric acid with alcohols, which constitute addition products of about 2–15 molecules of ethylene oxide and/or propylene oxide onto fatty alcohols having 8 to 22 carbon atoms.

Preferred anionic surfactants are alkyl sulfates, alkylpolyglycol ether sulfates and ether carboxylic acids having 10 to 18 carbon atoms in the alkyl group and up to 12 glycol ether groups in the molecule, and in particular salts of saturated and in particular unsaturated $C_8$–$C_{22}$-carboxylic acids, such as oleic acid, stearic acid, isostearic acid and palmitic acid.

Nonionogenic surfactants comprise, as hydrophilic group, e.g. a polyol group, a polyalkylene glycol ether group or a combination of polyol and polyglycol ether group. Such compounds are, for example, addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12}$–$C_{22}$-fatty acid mono- and diesters of addition products of from 1 to 30 mol of ethylene oxide onto glycerol, $C_8$–$C_{22}$-alkyl mono- and oligoglycosides and ethoxylated analogs thereof, and addition products of from 5 to 60 mol of ethylene oxide onto castor oil and hydrogenated castor oil.

Preferred nonionic surfactants are alkyl polyglycosides of the general formula $R^1O$-$(Z)_x$. These compounds are characterized by the following parameters.

The alkyl radical $R^1$ comprises 6 to 22 carbon atoms and may either be linear or branched. Preference is given to primary aliphatic radicals which are linear or methyl-branched in the 2 position. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. When using so-called "oxo alcohols" as starting materials, compounds with an uneven number of carbon atoms in the alkyl chain predominate.

The alkyl polyglycosides which can be used according to the invention can, for example, comprise only one particular alkyl radical $R^1$. Usually, however, these compounds are prepared starting from natural fats and oils or mineral oils. In this case, the alkyl radicals R present are mixtures corresponding to the starting compounds and corresponding to the particular work-up of these compounds.

Particular preference is given to those alkyl polyglycosides in which $R^1$ consists
essentially of $C_8$- and $C_{10}$-alkyl groups,
essentially of $C_{12}$- and $C_{14}$-alkyl groups,
essentially of $C_8$- to $C_{16}$-alkyl groups, or
essentially of $C_{12}$- to $C_{16}$-alkyl groups.

Sugar building blocks Z which may be used are any mono- or oligosaccharides. Usually, sugars with 5 or 6 carbon atoms and the corresponding oligosaccharides are used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention comprise, on average, 1.1 to 5 sugar units. Alkyl polyglycosides with x values of from 1.1 to 1.6 are preferred. Very particular preference is given to alkyl glycosides in which x is 1.1 to 1.4.

Besides their surfactant effect, the alkyl glycosides can also serve to improve the fixing of fragrance components on the hair. Thus, if an effect of the perfume oil on the hair which lasts beyond the duration of the hair treatment is desired, the person skilled in the art will preferably have recourse to this class of substance as further ingredient of the preparations according to the invention.

The alkoxylated homologs of the specified alkyl polyglycosides can also be used according to the invention. These homologs can on average contain up to 10 ethylene oxide and/or propylene oxide units per alkyl glycoside unit.

In addition, zwitterionic surfactants can be used, in particular as cosurfactants. Zwitterionic surfactants is the term used to refer to those surface-active compounds which carry at least one quaternary ammonium group and at least one $—COO^{(-)}$ or $—SO_3^{(-)}$ group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxymethylimidazolines having in each case 8 to 18 carbon atoms in the alkyl or acyl group, and cocoacylaminoethylhydroxyethyl carboxymethyl glycinate. A preferred zwitterionic surfactant is the fatty acid amide derivative known under the INCI name Cocamidopropyl Betaine.

Likewise particularly suitable as cosurfactants are ampholytic surfactants. Ampholytic surfactants are understood as meaning those surface-active compounds which, apart from a $C_8$–$C_{18}$-alkyl or acyl group, contain at least one free amino group and at least one $—COOH$ or $—SO_3H$ group in the molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

The cationic surfactants used according to the invention are, in particular, those of the quaternary ammonium compound type, the esterquat type and the amidoamine type.

Preferred quaternary ammonium compounds are ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the abovementioned surfactants preferably have 10 to 18 carbon atoms.

Esterquats are known substances which contain both at least one ester function and also at least one quaternary ammonium group as structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, an N,N-bis(2-palmitoyloxyethyl)dimethylammonium chloride, and Dehyquart® F-75 and Dehyquart® AU-35 are examples of such esterquats.

The alkylamidoamines are usually prepared by amidation of natural or synthetic fatty acids and fatty acid cuts with dialkylaminoamines. A compound from this group of substance which is particularly suitable according to the invention is the stearamidopropyldimethylamine available commercially under the name Tegoamid® S 18.

Further cationic surfactants which can be used according to the invention are the quaternized protein hydrolyzates.

Likewise suitable according to the invention are cationic silicone oils, such as, for example, the commercially available products Q2-7224 (manufacturer: Dow Corning; a stabilized trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80).

One example of a quaternary sugar derivative which can be used as cationic surfactant is the commercial product Glucquat® 100, according to INCI nomenclature a "Lauryl Methyl Gluceth-10 Hydroxypropyl Dimonium Chloride".

The compounds with alkyl groups used as surfactant may each be individual substances. However, it is usually preferred to start from natural vegetable or animal raw materials during the preparation of these substances, resulting in mixtures of substances with varying alkyl chain lengths which depend on the particular raw material.

The surfactants which constitute addition products of ethylene oxide and/or propylene oxide onto fatty alcohols or derivatives of these addition products and may be used are either products with a "normal" homolog distribution, or those with a narrowed homolog distribution. "Normal" homolog distribution is understood here as meaning mixtures of homologs which are obtained when reacting fatty alcohol and alkylene oxide using alkali metals, alkaline earth metal hydroxides or alkali metal alkoxides as catalysts. Narrowed homolog distributions, by contrast, are obtained if, for example, hydrotalcites, alkaline earth metal salts of ethercarboxylic acids, alkaline earth metal oxides, hydroxides or alkoxides are used as catalysts. Use of products with a narrowed homolog distribution may be preferred.

In addition, the colorants according to the invention can comprise further active ingredients, auxiliaries and additives, such as, for example,

- nonionic polymers, such as, for example, vinylpyrrolidone/vinyl acrylate copolymers, polyvinylpyrrolidone and vinylpyrrolidone/vinyl acetate copolymers and polysiloxanes,
- cationic polymers, such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidone copolymers quaternized with diethyl sulfate, vinylpyrrolidone-imidazolinum methochloride copolymers and quaternized polyvinyl alcohol,
- zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers,
- anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers,
- thickeners, such as agar agar, guar gum, alginates, xanthan gum, gum arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol,
- structurants, such as maleic acid and lactic acid,
- hair-conditioning compounds, such as phospholipids, for example soya lecithin, egg lecithin and cephalins,
- protein hydrolyzates, in particular elastin, collagen, keratin, milk protein, soya protein and wheat protein hydrolyzates, their condensation products with fatty acids, and quaternized protein hydrolyzates,
- perfume oils, dimethyl isosorbide and cyclodextrins,
- solvents and solubilizers, such as ethanol, isopropanol, ethylene glycol, propylene glycol, glycerol and diethylene glycol,
- active ingredients which improve the fiber structure, in particular mono-, di- and oligosaccharides, such as, for example, glucose, galactose, fructose, fruit sugar and lactose,
- quaternized amines, such as methyl-1-alkylamidoethyl-2-alkylimidazolium methosulfate
- antifoams, such as silicones,
- dyes for coloring the agent,
- antidandruff active ingredients, such as piroctone olamine, zinc omadine and climbazole,
- photoprotective agents, in particular derivatized benzophenones, cinnamic acid derivatives and triazines,
- substances for adjusting the pH, such as, for example, customary acids, in particular food acids and bases,
- active ingredients, such as allantoin, pyrrolidonecarboxylic acids and salts thereof, and bisabolol,
- vitamins, provitamins and vitamin precursors, in particular those of groups A, $B_3$, $B_5$, $B_6$, C, E, F and H,
- plant extracts, such as the extracts from green tea, oak bark, stinging nettle, hamamelis, hops, camomile, burdock, horsetail, hawthorn, lime blossom, almond, aloe vera, spruce needle, roast chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, myristum, ginseng and root ginger,
- cholesterol,
- consistency regulators such as sugar esters, polyol esters or polyol alkyl ethers,
- fats and waxes, such as spermaceti, beeswax, montan wax and paraffins,
- fatty acid alkanolamides,
- complexing agents, such as EDTA, NTA, β-alanine-diacetic acid and phosphonic acids,
- swelling and penetration substances, such as glycerol, propylene glycol monoethyl ether, carbonates, hydrogencarbonates, guanidines, ureas, and primary, secondary and tertiary phosphates,
- opacifiers, such as latex, styrene/PVP and styrene/acrylamide copolymers
- pearlizing agents, such as ethylene glycol mono- and distearate and PEG-3 distearate,
- pigments,
- stabilizers for hydrogen peroxide and other oxidizing agents,
- propellants, such as propane-butane mixtures, $N_2O$, dimethyl ether, $CO_2$ and air,
- antioxidants.

With regard to further optional components and the amounts used of these components, reference is made expressly to the relevant handbooks known to the person skilled in the art, e.g. Kh. Schrader, Grundlagen und Rezepturen der Kosmetika [Fundamentals and formulations of cosmetics], $2^{nd}$ edition, Huthig Buch Verlag, Heidelberg, 1989.

The agents according to the invention comprise the dye precursors preferably in a suitable aqueous, alcoholic or aqueous-alcoholic carrier. For the purpose of hair coloring, such carriers are, for example, creams, emulsions, gels or else surfactant-containing foaming solutions, such as, for example, shampoos, foam aerosols or other preparations which are suitable for use on the hair. It is, however, also conceivable to integrate the dye precursors into a pulverulent or else tablet-like formulation.

For the purposes of the present invention, aqueous-alcoholic solutions are aqueous solutions comprising 3 to 70% by weight of a $C_1$–$C_4$-alcohol, in particular ethanol and isopropanol. The agents according to the invention can additionally comprise further organic solvents, such as, for example, methoxybutanol, benzyl alcohol, ethyl diglycol or 1,2-propylene glycol. Preference here is given to all water-soluble organic solvents.

The actual oxidative coloring of the fibers can in principle take place with atmospheric oxygen. However, preference is given to using a chemical oxidizing agent, especially if a lightening effect on human hair is desired besides the coloring. Suitable oxidizing agents are persulfates, chlorites and in particular hydrogen peroxide or its addition products onto urea, melamine and sodium borate. According to the invention, however, the oxidation colorant can also be applied to the hair together with a catalyst which activates the oxidation of the dye precursors, e.g. by atmospheric oxygen. Such catalysts are, for example, metal ions, iodides, quinones or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Of particular suitability here are $Zn^{2+}$, $Cu^{2+}$ and $Mn^{2+}$. The metal ions can in principle be used in the form of any physiologically compatible salt or in the form of a complex. Preferred salts are the acetates, sulfates, halides, lactates and tartrates. By using these metal salts it is possible both to accelerate the formation of the coloration and also to influence the color shade in a targeted manner.

Suitable enzymes are, for example, peroxidases, which can significantly increase the effect of small amounts of hydrogen peroxide. Also suitable according to the invention are those enzymes which directly oxidize the oxidation dye precursors with the help of atmospheric oxygen, such as, for example, the laccases, or in situ produce small amounts of hydrogen peroxide and in so doing biocatalytically activate the oxidation of the dye precursors. Particularly suitable catalysts for the oxidation of the dye precursors are the so-called 2-electron oxidoreductases in combination with the substrates specific for this purpose, e.g.

pyranose-oxidase and e.g. D-glucose or galactose,
glucose-oxidase and D-glucose,
glycerol-oxidase and glycerol,
pyruvate-oxidase and pyruvic acid or salts thereof,
alcohol-oxidase and alcohol (MeOH, EtOH),
lactate-oxidase and lactic acid and salts thereof,
tyrosinase-oxidase and tyrosine,
uricase and uric acid or salts thereof,
choline oxidase and choline,
amino acid-oxidase and amino acids.

The actual hair colorant is expediently prepared directly prior to use by mixing the preparation of the oxidizing agent with the preparation comprising the dye precursors. The resulting ready-to-use hair-coloring preparation should preferably have a pH in the range from 6 to 12. Application of the hair colorant in a weakly alkaline medium is particularly preferred. According to the invention, it may be particularly preferred if the colorants according to the invention have an alkaline pH at the time of application. A pH between 9 and 12 is particularly preferred. The application temperatures can be in a range between 15 and 40° C. After a contact time of 5 to 45 minutes, the hair colorant is removed from the hair to be colored by rinsing. After-washing with a shampoo is dispensed with if a carrier with a high content of surfactant, e.g. a coloring shampoo, has been used.

Particularly in the case of hair which is difficult to color, the preparation with the dye precursors can, however, also be applied to the hair without prior mixing with the oxidation component. After a contact time of 20 to 30 minutes—if appropriate after an intermediate rinse—the oxidation component is then applied. After a further contact time of 10 to 20 minutes, the hair is then rinsed and if desired shampooed. With this embodiment, according to a first variant in which the prior application of the dye precursors is intended to bring about better penetration into the hair, the corresponding agent is adjusted to a pH of from about 4 to 7. According to a second variant, the aim is firstly an air oxidation, the applied agent preferably having a pH of from 7 to 10. For the subsequent accelerated postoxidation, it may be preferred to use peroxydisulfate solutions which have been rendered acidic as oxidizing agents.

The present application secondly provides the use of the m-phenylenediamine derivatives according to the invention for coloring keratin fibers.

The present invention thirdly relates to the use of the m-phenylenediamine derivatives according to the invention in oxidative colorants for achieving red shades.

The present invention fourthly relates to a method of coloring keratin fibers in which a hair colorant according to the invention is applied to the fibers and, after a contact time, is rinsed out again.

The present invention fifthly relates to m-phenylenediamine derivatives of the formula (I)

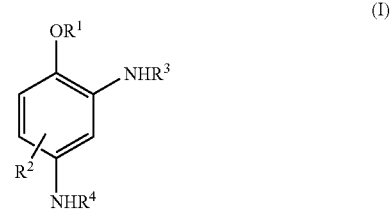

(I)

where $R^1$ is a $C_1$- to $C_4$-alkyl group or a $C_1$- to $C_4$-monohydroxyalkyl group,
$R^2$ is a methyl or an ethyl group, and
$R^3$ and $R^4$, independently of one another, are a branched or unbranched $C_2$- to $C_6$-hydroxyalkyl group.

2,4-Bis[(2-hydroxyethyl)amino]-6-methylanisole is an m-phenylenediamine which is particularly preferred according to the invention.

The present invention sixthly relates to the first intermediates of the synthesis of the m-phenylenediamines according to the invention, in particular bis(2-chloroethyl) (4-methoxy-5-methyl-1,3-phenylene)-biscarbamate.

The present invention seventhly relates to the second intermediates of the synthesis of the m-phenylenediamines according to the invention, in particular 3,3'-(4-methoxy-5-methyl-1,3-phenylene)bis(1,3-oxazolidin-2-one).

WORKING EXAMPLES

1 Syntheses 1.1 2,4-Bis[(2-hydroxyethyl)amino]-6-methylanisole

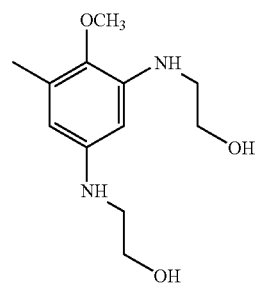

1.1.1 2,4-Dinitro-6-methylanisole 1 l of fuming nitric acid was initially introduced at 5–10° C., and 100 g of 2-methylanisole were added dropwise with stirring (about 45 min). The mixture was then after-stirred for 30 min and then poured onto ice. The precipitate was filtered off and washed with a large amount of water. The mother liquor was diluted with 2×500 ml of water and the precipitates were filtered off with suction. The combined precipitates were then washed until neutral with 2×400 ml of sodium carbonate solution and water and dried overnight under reduced pressure.

Yield: 107 g (62%)

Melting point: δ 66–68° C.

1.1.2 2,4-Diamino-6-methylanisole dihydrochloride 105 g of 2,4-dinitro-6-methylanisole, 1.35 l of ethanol, 150 ml of water and 1 g of Pd/C (5% strength) were initially introduced into the autoclave and hydrogenated at 50° C. with a hydrogen pressure of 50 bar for 12 h. Subsequently, the mixture was cooled and then poured into 1.0 l of semiconcentrated HCl. The catalyst was filtered off, and the filtrate was evaporated to dryness on a rotary evaporator. The residue was extracted by boiling with 2×150 ml of ethanol, filtered off and dried overnight under reduced pressure.

Yield: 74 g (67%)

1.1.3 Bis(2-chloroethyl) (4-methoxy-5-methyl-1,3-phenylene)biscarbamate 56 g of 2,4-diamino-6-methylanisole dihydrochloride and 134 g of calcium carbonate were initially introduced into 1 l of dioxane and heated to 90° C. Within 15 min, 80 g of 2-chloroethyl chloroformate were added and the mixture was stirred for a further 4 h at this temperature. Subsequently, the mixture was left to cool, and the mineral salts were filtered off. The filtrate was poured onto iced water, and the mixture was extracted several times with ethyl acetate. The combined ethyl acetate phases were then evaporated to dryness on a Rotavapor, giving pale brown crystals.

Yield: 60 g (75%)

Melting point: 63–65° C.

1.1.4 3,3'-(4-methoxy-5-methyl-1,3-phenylene)bis(1,3-oxazolidin-2-one)

200 ml of sodium hydroxide solution (20% strength) were initially introduced and heated to 45° C. Subsequently, 59 g of bis(2-chloroethyl) (4-methoxy-5-methyl-1,3-phenylene) biscarbamate were added in portions and the mixture was diluted with 200 ml of dioxane. The mixture was after-stirred for a further 2 h at 45° C. After stirring overnight at room temperature, the mixture was poured onto ice, and the mixture was neutralized with hydrochloric acid. The precipitated product was filtered off with suction and dried overnight under reduced pressure.

Yield: 34 g (73%)

Melting point: 153–156° C.

1.1.5 2,4-Bis[(2-hydroxyethyl)amino]-6-methylanisole 33.5 g of 3,3'-(4-methoxy-5-methyl-1,3-phenylene)bis-(1,3-oxazolidin-2-one) were heated under reflux in 500 ml of 20% strength KOH for 10 h. The mixture was cooled to room temperature and poured onto 1.5 l of iced water. The mixture was then neutralized with HCl and extracted several times with ethyl acetate. The combined ethyl acetate phases were evaporated on a Rotavapor and then distilled in a Kugelrohr (250–290° C., 0.08 mbar).

Yield: 7.8 g (30%)

2 Colorations

2.1 Experimental Procedure

To prepare the coloring cream, 50 g of a cream base are weighed into a 250 ml beaker and melted at 80° C. The cream base used had the following composition:

| | |
|---|---|
| Hydrenol ® D[1] | 17.0% by weight |
| Lorol ® tech.[2] | 4.0% by weight |
| Texapon ® NSO[3] | 40.0% by weight |
| Dehyton ® K[4] | 25.0% by weight |
| Eumulgin ® B2[5] | 1.5% by weight |
| Water | 12.5% by weight |

[1]$C_{16-18}$-fatty alcohol (INCI name: Cetearyl alcohol) (Cognis)
[2]$C_{12-18}$-fatty alcohol (INCI name: Coconut alcohol) (Cognis)
[3]Lauryl ether sulfate, sodium salt (about 27.5% active substance; INCI name: Sodium Laureth Sulfate) (Cognis)
[4]N,N-Dimethyl-N-($C_{8-18}$-cocamidopropyl)ammoniumaceto-betaine (about 30% active substance; INCI name: Aqua (water), Cocamidopropyl Betaine) (Cognis)
[5]Cetylstearyl alcohol with about 20 EO units (INCI name: Ceteareth-20) (Cognis)

In each case, 1/400 mol of the developer or coupler component was suspended or dissolved with heating separately in distilled water. Ammonia (<1 ml; 25% strength ammonia solution) was then added until the pH was between 9 and 10.

The dissolved dye precursors were incorporated one after the other into the hot cream. Then, distilled water was used to make up to 97 g and ammonia was used to establish a pH of 9.5. After making up to 100 g with distilled water, the mixture was stirred under cold conditions (<30° C.), whereupon a homogeneous cream was formed.

For the colorations (unless noted otherwise) in each case 25 g of coloring cream were mixed with 25 g of the following oxidizing agent preparation.

| | |
|---|---|
| Dipicolinic acid | 0.1% by weight |
| Sodium pyrophosphate | 0.03% by weight |
| Turpinal ® SL[6] | 1.50% by weight |
| Texapon ® N28[7] | 2.00% by weight |
| Acrysol ® 22[8] | 0.60% by weight |
| Hydrogen peroxide, 50% strength | 12.00% by weight |
| Sodium hydroxide solution, 45% strength | 0.80% by weight |
| Water | ad 100% by weight |

[6]1-Hydroxyethane-1,1-diphosphonic acid (about 58–61% active substance content; INCI name: Etidronic Acid, Aqua (Water)) (Solutia)
[7]Lauryl ether sulfate sodium salt (at least 26.5% active substance content; INCI name: Sodium Laureth Sulfate) (Cognis)
[8]Acrylic polymer (about 29.5–30.5% solids in water; INCI name: Acrylates/Steareth-20 Methacrylate Copolymer)

A hair tress (80% gray; 330 mg to 370 mg in weight) was placed into each of the mixtures obtained in this way. The mixtures and the hair tresses were then each placed onto an watchglass and the hair tresses were thoroughly embedded into the coloring creams. After a contact time of 30 minutes (±1 minute) at room temperature, the hair tresses were removed[9] and washed with an aqueous Texapon® EVR solution until the color excess was removed. The hair tresses were dried under air and their color shade was determined under a daylight lamp (color testing instrument HE240A) and noted (Taschenlexikon der Farben [Pocket lexicon of colors], A. Kornerup & J. H. Wanscher, 3rd unrevised edition 1981, MUSTER-SCHMIDT Verlag; Zurich, Göttingen).

[9] Lauryl ether sulfate sodium salt with special additives (about 34 to 37% active substance content; INCI name: Sodium Lauryl Sulfate, Sodium Laureth Sulfate, Lauramide MIPA, Cocamide MEA, Glycol Stearate, Laureth-10) (Cognis)

The results obtained in the coloring investigations are listed in the tables below.

2.2. Colorations with 2,4-bis[(2-hydroxyethyl)amino]-6-methylanisole

| Developer component | Coloration |
| --- | --- |
| p-Tolylenediamine sulfate | bordeaux red |
| 2,4,5,6-Tetraaminopyrimidine sulfate | pepper red |
| p-Aminophenol | cockscomb red |
| 4,5-Diamino-1-(2-hydroxyethyl)pyrazole sulfate | dark violet |
| 2-(2,5-Diaminophenyl)ethanol sulfate | gray-ruby |
| 4-Amino-3-methylphenol | brown-red |
| 4-Amino-2-[(5-amino-2-hydroxyphenyl)-methyl]phenol dihydrochloride | brown-violet |

2.3 Colorations with 2,4-di(β-hydroxyethylamino)-1-methoxybenzene (Coupler Component of the Prior Art)

| Developer component | Coloration |
| --- | --- |
| p-Tolylenediamine sulfate | black-blue |
| 2,4,5,6-Tetraaminopyrimidine sulfate | nordic blue |
| 2-(2,5-diaminophenyl)ethanol sulfate | marine blue |

2.4 Colorations with 4,7-bis(2-hydroxyethylamino)-2,3-dihydroxybenzofuran (Structurally Related Coupler Component)

| Developer component | Coloration |
| --- | --- |
| p-Tolylenediamine sulfate | gray-brown |
| 2,4,5,6-Tetraaminopyrimidine sulfate | cinnamon brown |
| 2-(2,5-diaminophenyl)ethanol sulfate | gray-brown |

The colorations of the coupler component according to the invention 2,4-bis[(2-hydroxyethyl)amino]-6-methylanisole (point 2.2) have been shifted significantly into the red range compared with the colorations of a coupler component of the prior art (point 2.3) and of a structurally related compound (point 2.4).

3 Further Colorations

3.1 Formulation 1

| Raw material | % by wt. |
| --- | --- |
| Fatty alcohol mixture $C_{10}$–$C_{22}$ | 6.0 |
| Stenol ® 1618[10] | 3.5 |
| Kokoslorol ®[11] | 1.5 |
| Behenyl alcohol | 1.0 |
| Eumulgin ® B 1[12] | 0.3 |
| Eumulgin ® B 2 | 0.3 |
| Texapon ® NSO | 10.0 |
| Dehyton ® K | 5.0 |
| Polymer JR ® 400[13] | 0.3 |
| Gafquat ® 755[14] | 0.3 |
| Celquat ® L200[15] | 0.1 |
| Ascorbic acid | 0.2 |
| Sodium metabisulfite | 0.3 |
| Ammonium sulfate | 0.4 |
| Hydroxyethanediphosphonic acid | 0.2 |
| Waterglass solution, 40% | 0.5 |
| Perfume oil | 0.3 |
| 1,10-Bis(2,5-diaminophenyl)-1,4,7,19-tetraoxadecane tetrahydrochloride | 0.05 |
| p-Tolylenediamine sulfate | 0.22 |
| N,N-Bis(2'-hydroxyethyl)-p-phenylenediamine sulfate | 0.15 |
| 2-(2'-Hydroxyethyl)-p-phenylenediamine sulfate | 0.24 |
| Bis(5-amino-2-hydroxyphenyl)methane dihydrochloride | 0.17 |
| 2,4-Bis(2'-hydroxyethyl)amino-6-methyl-anisole | 0.50 |
| 2,6-Bis[(2'-hydroxyethyl)]amino-4-methyl-anisole | 0.05 |
| Ammonia, 25% strength | ad pH 10 |
| Water | ad 100 |

[10]$C_{16-18}$-fatty alcohol (INCI name: Cetearyl Alcohol) (Cognis)
[11]$C_{12-18}$-fatty alcohol (INCI name: Coconut Alcohol) (Cognis)
[12]Cetylstearyl alcohol with about 12 EO units (INCI name: Ceteareth-12) (Cognis)
[13]Quaternized hydroxyethylcellulose (INCI name: Polyquaternium-10) (Amerchol)
[14]Dimethylaminoethyl methacrylate-vinylpyrrolidone copolymer, quaternized with diethyl sulfate (about 19% solids in water; INCI name: Polyquaternium-11) (ISP)
[15]Quaternized cellulose derivative (INCI name: Polyquaternium-4) (National Starch)

3.2 Formulation 2

| Raw material | % by wt. |
| --- | --- |
| Fatty alcohol mixture $C_{10}$–$C_{22}$ | 6.0 |
| Eumulgin ® B 1 | 0.3 |
| Eumulgin ® B 2 | 0.3 |
| Texapon ® NSO | 10.0 |
| Dehyton ® K | 5.0 |
| Polymer JR ® 400 | 0.3 |
| Gafquat ® 755 | 0.3 |
| Celquat ® L 200 | 0.1 |
| Ascorbic acid | 0.2 |
| Sodium metabisulfite | 0.3 |
| Ammonium sulfate | 0.4 |
| Hydroxyethanediphosphonic acid | 0.2 |
| Waterglass solution, 40% | 0.5 |
| Perfume oil | 0.3 |
| 1,3-N,N'-Bis(2'-hydroxyethyl)-N,N'-bis(4-aminophenyl)diaminopropan-2-ol tetrahydrochloride | 0.1 |
| p-Phenylenediamine dihydrochloride | 0.09 |
| p-Tolylenediamine sulfate | 0.11 |

-continued

| Raw material | % by wt. |
|---|---|
| 4-Aminophenol | 0.03 |
| 4-Amino-3-methylphenol | 0.01 |
| 4-Amino-2-aminomethylphenol dihydrochloride | 0.01 |
| 4-Amino-2-[(diethylamino)methyl]phenol dihydrochloride | 0.01 |
| Bis(5-amino-2-hydroxyphenyl)methane dihydrochloride | 0.40 |
| 4,5-Diamino-2-(2'-hydroxyethyl)pyrazole sulfate | 0.24 |
| 2,4-Bis(2'-hydroxyethyl)amino-6-methylanisole | 0.11 |
| 2,6-Bis[(2'-hydroxyethyl)]amino-4-methylanisole | 0.65 |
| Ammonia, 25% strength | ad pH 10 |
| Water | ad 100 |

3.3 Formulation 3

| Raw material | % by wt. |
|---|---|
| Fatty alcohol mixture $C_{10}$–$C_{22}$ | 6.0 |
| Eumulgin ® B 1 | 0.3 |
| Eumulgin ® B 2 | 0.3 |
| Texapon ® NSO | 10.0 |
| Dehyton ® K | 5.0 |
| Polymer JR ® 400 | 0.3 |
| Gafquat ® 755 | 0.3 |
| Celquat ® L 200 | 0.1 |
| Ascorbic acid | 0.2 |
| Sodium metabisulfite | 0.3 |
| Ammonium sulfate | 0.4 |
| Hydroxyethanediphosphonic acid | 0.2 |
| Waterglass solution, 40% | 0.5 |
| Perfume oil | 0.3 |
| 2,4,5,6-Tetraaminopyrimidine sulfate | 0.88 |
| 4-Hydroxy-2,5,6-triaminopyrimidine sulfate | 0.07 |
| 2,4-Bis(2'-hydroxyethyl)amino-6-methylanisole | 0.34 |
| 2,6-Bis[(2'-hydroxyethyl)]amino-4-methylanisole | 0.36 |
| Resorcinol | 0.02 |
| 2-Methylresorcinol | 0.08 |
| 4-Chlororesorcinol | 0.01 |
| Resorcinol monomethyl ether | 0.01 |
| Ammonia, 25% strength | ad pH 10 |
| Water | ad 100 |

3.4 Formulation 4

| Raw material | % by wt. |
|---|---|
| Fatty alcohol mixture $C_{10}$–$C_{22}$ | 10.0 |
| Texapon ® K 14 S 70 C[16] | 2.5 |
| Plantaren ® 1200 UP[17] | 2.0 |
| Akypo Soft ® 45 NV[18] | 12.0 |
| Eutanol ® G[19] | 1.0 |
| Eumulgin ® B 1 | 0.5 |
| Eumulgin ® B 2 | 0.5 |
| Polymer W 37194[20] | 2.0 |
| Cosmedia Guar ® C 261[21] | 0.2 |
| Mirapol ® A 15[22] | 0.5 |
| Ascorbic acid | 0.2 |
| EDTA disodium salt | 0.1 |
| Sodium metabisulfite | 0.3 |
| Ammonium sulfate | 0.5 |
| Perfume oil | 0.4 |
| Promois ® WK[23] | 2.0 |
| Dow Corning ® Q2-1401[24] | 0.2 |
| Gluadin ® WQ[25] | 1.0 |
| p-Tolylenediamine sulfate | 0.55 |
| N,N-Bis(2'-hydroxyethyl)-p-phenylenediamine sulfate | 0.94 |
| 4-Amino-3-methylphenol | 0.03 |
| 2,4,5,6-Tetraaminopyrimidine sulfate | 1.0 |
| 2,4-Bis(2'-hydroxyethyl)amino-6-methylanisole | 0.10 |
| 2,6-Bis[(2'-hydroxyethyl)]amino-4-methylanisole | 0.05 |
| Resorcinol | 0.11 |
| 2-Methylresorcinol | 0.54 |
| 3-Aminophenol | 0.06 |
| 1,3-Bis(2',4'-diaminophenoxy)propane tetrahydrochloride | 0.001 |
| 2-Amino-3-hydroxypyridine | 0.30 |
| 2-Methylamino-3-amino-6-methoxypyridine | 0.001 |
| 2,7-Dihydroxynaphthalene | 0.03 |
| Ammonia, 25% strength | ad pH 10 |
| Water | ad 100 |

[16]Lauryl myristyl ether sulfate sodium salt (about 68% to 73% active substance content; INCI name: Sodium Myreth Sulfate) (Cognis)
[17]$C_{12}$–$C_{16}$-fatty alcohol 1,4-glucoside unpreserved, boron-free, about 50–53% active substance) (Cognis Corporation (Emery))
[18]Lauryl alcohol 4.5 EO acetic acid sodium salt (at least 21% active substance content; INCI name: Sodium Laureth-6 Carboxylate) (Chem-Y)
[19]2-Octyldodecyl alcohol (INCI name: Octyldodecanol) (Cognis)
[20]about 20% by weight active substance content in water; INCI name: Acrylamidopropyltrimonium Chloride/Acrylates Copolymer (Stockhausen)
[21]Guar hydroxypropyltrimethylammonium chloride (at least 93% solids; INCI name: Guar Hydroxypropyltrimonium Chloride) (Cognis CorporationCosmedia)
[22]Poly[N-(3-(dimethylammonium)propyl]-N'-[3-ethyleneoxydimethylammonium)propyl]urea dichloride (about 64% solids in water; INCI name: Polyquaternium-2) (Rhodia)
[23]Keratin hydrolyzate (INCI name: Aqua (Water), Hydrolyzed Keratin, methylparaben, Propylparaben) (Seiwa (Interorgana))
[24]Dimethylcyclosiloxane dimethylpolysiloxanol mixture (about 13% solids; INCI name: Cyclomethicone, Dimethiconol) (Dow Corning)
[25]Wheat protein hydrolyzate (about 31–35% solids; INCI name: Aqua (Water), Laurdimonium Hydroxypropyl Hydrolyzed Wheat Protein, Ethylparaben, Methylparaben) (Cognis)

3.5 Formulation 5

| Raw material | % by wt. |
|---|---|
| Fatty alcohol mixture $C_{10}$–$C_{22}$ | 10.0 |
| Texapon ® K 14 S 70 C | 2.5 |
| Plantaren ® 1200 UP | 2.0 |
| Akypo Soft ® 45 NV | 12.0 |
| Eutanol ® G | 1.0 |
| Eumulgin ® B 1 | 0.5 |
| Eumulgin ® B 2 | 0.5 |
| Polymer W 37194 | 2.0 |
| Cosmedia Guar ® C 261 | 0.2 |
| Mirapol ® A 15 | 0.5 |
| Ascorbic acid | 0.2 |
| EDTA disodium salt | 0.1 |
| Sodium metabisulfite | 0.3 |
| Ammonium sulfate | 0.5 |
| Perfume oil | 0.4 |
| Promois ® WK | 2.0 |
| Dow Corning ® Q2-1401 | 0.2 |
| Gluadin ® WQ | 1.0 |
| p-Phenylenediamine dihydrochloride | 0.10 |
| N,N-Bis(2'-hydroxyethyl)-p-phenylenediamine sulfate | 0.16 |

-continued

| Raw material | % by wt. |
|---|---|
| 2-(2'-Hydroxyethyl)-p-phenylenediamine sulfate | 0.34 |
| 4,5-Diamino-2-(2'-hydroxyethyl)pyrazole sulfate | 0.30 |
| 2,4-Bis(2'-hydroxyethyl)amino-6-methylanisole | 0.05 |
| 2,6-Bis[(2'-hydroxyethyl)]amino-4-methylanisole | 0.10 |
| Resorcinol | 0.09 |
| 5-(2'-Hydroxyethyl)amino-2-methylphenol | 0.07 |
| 3-Amino-2-chloro-6-methylphenol | 0.20 |
| 2,4-Diaminophenoxyethanol sulfate | 0.01 |
| 1,3-Bis(2',4'-diaminophenoxy)propane tetrahydrochloride | 0.01 |
| 2-Amino-3-hydroxypyridine | 0.09 |
| 3,5-Diamino-2,6-dimethoxypyridine | 0.005 |
| 2,6-Bis(2'-hydroxyethylamino)toluene | 0.1 |
| 5,6-Dihydroxyindoline hydrobromide | 0.05 |
| 4-Amino-2-nitrodiphenylamine 2'-carboxylic acid | 0.05 |
| Ammonia, 25% strength | ad pH 10 |
| Water | ad 100 |

3.6 Formulation 6

| Raw material | % by wt. |
|---|---|
| Fatty alcohol mixture $C_{10}$–$C_{22}$ | 10.0 |
| Texapon ® K 14 S 70 C | 2.5 |
| Plantaren ® 1200 UP | 2.0 |
| Akypo Soft ® 45 NV | 12.0 |
| Eutanol ® G | 1.0 |
| Eumulgin ® B 1 | 0.5 |
| Eumulgin ® B 2 | 0.5 |
| Polymer W 37194 | 2.0 |
| Cosmedia Guar ® C 261 | 0.2 |
| Mirapol ® A 15 | 0.5 |
| Ascorbic acid | 0.2 |
| EDTA disodium salt | 0.1 |
| Sodium metabisulfite | 0.3 |
| Ammonium sulfate | 0.5 |
| Perfume oil | 0.4 |
| Promois ® WK | 2.0 |
| Dow Corning ® Q2-1401 | 0.2 |
| Gluadin ® WQ | 1.0 |
| 2-(2'-Hydroxyethyl)-p-phenylenediamine sulfate | 0.83 |
| 4-Aminophenol | 0.02 |
| 4-Amino-3-methylphenol | 0.01 |
| Bis(5-amino-2-hydroxyphenyl)methane dihydrochloride | 0.10 |
| 2,4,5,6-Tetraaminopyrimidine sulfate | 1.10 |
| 4-Hydroxy-2,5,6-triaminopyrimidine sulfate | 0.15 |
| 2,4-Bis(2'-hydroxyethyl)amino-6-methylanisole | 0.25 |
| 2,6-Bis[(2'-hydroxyethyl)]amino-4-methylanisole | 0.05 |
| Resorcinol | 0.1 |
| 2-Methylresorcinol | 0.60 |
| 4-Chlororesorcinol | 0.03 |
| 3-Aminophenol | 0.004 |
| 5-Amino-2-methylphenol | 0.03 |
| 3-Amino-2-chloro-6-methylphenol | 0.03 |
| 2-Amino-3-hydroxypyridine | 0.24 |
| 2,6-Dihydroxy-3,4-dimethylpyridine | 0.10 |
| 2,7-Dihydroxynaphthalene | 0.02 |
| 1-Phenyl-3-methylpyrazol-5-one | 0.01 |
| Ammonia, 25% strength | ad pH 10 |
| Water | ad 100 |

3.7 Formulation 7

| Raw material | % by wt. |
|---|---|
| Stenol ® 1618 | 4.5 |
| Kokoslorol ® | 2.5 |
| Behenyl alcohol | 1.0 |
| Texapon ® NSO | 2.0 |
| Dehyton ® K | 1.0 |
| Potassium oleate | 2.0 |
| Potassium isostearate | 2.0 |
| Potassium myristate | 1.0 |
| Westvaco ® Diacid H240, K salt[26] | 2.0 |
| Merquat ® 550[27] | 0.2 |
| Luviquat ® FC 370[28] | 0.1 |
| Merquat ® 280[29] | 0.1 |
| Gafquat ® HS-100[30] | 0.1 |
| Ascorbic acid | 0.4 |
| Hydroxyethanediphosphonic acid | 0.2 |
| Perfume oil | 0.4 |
| p-Tolylenediamine sulfate | 0.10 |
| N,N-Bis(2'-hydroxyethyl)-p-phenylenediamino sulfate | 0.88 |
| 2-(2'-Hydroxyethyl)-p-phenylenediamine sulfate | 0.1 |
| 4,5-Diamino-2-(2'-hydroxyethyl)pyrazole sulfate | 0.72 |
| 2,4-Bis(2'-hydroxyethyl)amino-6-methylanisole | 0.68 |
| 2,6-Bis[(2'-hydroxyethyl)]amino-4-methylanisole | 0.72 |
| Resorcinol | 0.02 |
| 2-Methylresorcinol | 0.03 |
| 4-Chlororesorcinol | 0.02 |
| 5-Amino-2-methylphenol | 0.01 |
| 5-(2'-Hydroxyethyl) amino-2-methylphenol | 0.05 |
| 5-Amino-4-chloro-2-methylphenol | 0.24 |
| 3-Amino-2-chloro-6-methylphenol | 0.07 |
| 1-Naphthol | 0.01 |
| 1,5-Dihydroxynaphthalene | 0.05 |
| 2,6-Bis(2'-hydroxyethylamino)toluene | 0.15 |
| HC Red 1[31] | 0.05 |
| HC Red BN[32] | 0.05 |
| HC Red B 54[33] | 0.05 |
| Basic Red 51[34] | 0.05 |
| Ammonia, 25% strength | ad pH 10 |
| Water | ad 100 |

[26] 4-Hexyl-5(6)-carboxy-2-cyclohexen-1-octanoic acid potassium salt (about 41% active substance in water) (Westvaco Chemicals)
[27] Dimethyldiallylammonium chloride acrylamide copolymer (about 8.1–9.1% active substance in water; INCI name: Polyquaternium-7) (Ondeo-Nalco)
[28] Vinylimidazolium methochloride-vinylpyrrolidone copolymer (30:70) (38–42% solids in water; INCI name: Polyquaternium-16) (BASF)
[29] Dimethyldiallylammonium chloride-acrylic acid copolymer (about 35 active substance in water; INCI name: Polyquaternium-22) (Ondeo-Nalco)
[30] Vinylpyrrolidone, methacrylamidopropyltrimethyl-ammonium chloride copolymer (19–21% active substance in water; INCI name: polyquaternium-28) (ISP)
[31] 4-Amino-2-nitrodiphenylamine
[32] 4-[(3-Hydroxypropyl)amino]-3-nitrophenol
[33] 4-[(2-Hydroxyethyl)amino]-3-nitrophenol (INCI name: 3-Nitro-p-hydroxyethylaminophenol)
[34] Azo dye (CIBA)

3.8 Formulation 8

| Raw material | % by wt. |
|---|---|
| Stenol ® 1618 | 4.5 |
| Kokoslorol ® | 2.5 |
| Behenyl alcohol | 1.0 |
| Texapon ® NSO | 2.0 |

| Raw material | % by wt. |
|---|---|
| Dehyton ® K | 1.0 |
| Potassium oleate | 2.0 |
| Potassium isostearate | 2.0 |
| Potassium myristate | 1.0 |
| Westvaco ® Diacid H240, K salt | 2.0 |
| Merquat ® 550 | 0.2 |
| Luviquat ® FC 370 | 0.1 |
| Merquat ® 280 | 0.1 |
| Gafquat ® HS-100 | 0.1 |
| Ascorbic acid | 0.4 |
| Hydroxyethanediphosphonic acid | 0.2 |
| Perfume oil | 0.4 |
| 4-Amino-2-aminomethylphenol dihydrochloride | 0.05 |
| 4-Amino-2-[(diethylamino)methyl]phenol dihydrochloride | 0.05 |
| Bis(5-amino-2-hydroxyphenyl)methane dihydrochloride | 0.91 |
| 2,4,5,6-Tetraaminopyrimidine sulfate | 0.24 |
| 2,4-Bis(2'-hydroxyethyl)amino-6-methylanisole | 0.90 |
| 1,2,3,4-Tetrahydro-6-nitroquinoxaline | 0.05 |
| HC Yellow 5[35] | 0.05 |
| HC Red BN | 0.1 |
| 2-Ethylamino-4-nitro-6-chlorophenol | 0.05 |
| 4-Amino-3-nitrophenol | 0.05 |
| HC Red B 54 | 0.1 |
| Ammonia, 25% strength | ad pH 10 |
| Water | ad 100 |

[35]$N^1$-(2-Hydroxyethyl)-4-nitro-1,2-phenylenediamine

3.9 Formulation 9

| Raw material | % by wt. |
|---|---|
| Stenol ® 1618 | 6.0 |
| Kokoslorol ® | 6.0 |
| Eumulgin ® B 1 | 3.0 |
| Eumulgin ® B 2 | 3.0 |
| Eumulgin ® RH 40[36] | 1.0 |
| Polydiol ® 400[37] | 5.0 |
| Aminoxyd ® WS 35[38] | 1.0 |
| EDTA disodium salt | 0.1 |
| Natrosol ® 250 HHR[39] | 1.0 |
| Ascorbic acid | 0.1 |
| Hydroxyethanediphosphonic acid | 0.2 |
| Perfume oil | 0.3 |
| 2,4,5,6-Tetraaminopyrimidine sulfate | 1.19 |
| 2,4-Bis(2'-hydroxyethyl)amino-6-methylanisole | 0.23 |
| 2,6-Bis[(2'-hydroxyethyl)amino-4-methylanisole | 0.72 |
| 2-Methylresorcinol | 0.03 |
| 4-Chlororesorcinol | 0.02 |
| 2,6-Bis(2'-hydroxyethylamino)toluene | 0.21 |
| 1,2,3,4-Tetrahydro-6-nitroquinoxaline | 0.15 |
| HC Yellow | 0.05 |
| 4-Amino-3-nitrophenol | 0.02 |
| Basic Yellow 87[40] | 0.05 |
| Basic Orange 31[41] | 0.10 |
| Basic Red 51 | 0.05 |

| Raw material | % by wt. |
|---|---|
| Ammonia, 25% strength | ad pH 10 |
| Water | ad 100 |

[36]hydrogenated castor oil with about 40 EO units (INCI name: PEG-40 Hydrogenated Castor Oil) (Cognis)
[37]Polyethylene glycol (INCI name: PEG-8) (Cognis)
[38]N,N-Dimethyl-N($C_{8-18}$-cocoacylamidopropyl)amine N-oxide (about 35% active substance content in water; INCI name: Cocamidopropylamine Oxide) (Goldschmidt)
[39]Hydroxyethylcellulose (INCI name: Hydroxyethylcellulose) (Hercules)
[40]Methine dye (CIBA)
[41]Azo dye (CIBA)

3.10 Formulation 10

| Raw material | % by wt. |
|---|---|
| Edenor ® PK 1805[42] | 7.0 |
| Texapon ® NSO | 4.0 |
| Coconut fatty alcohol | 7.5 |
| Dehydrol ® LS 2[43] | 8.0 |
| Isopropanol | 14.5 |
| Sodium metabisulfite | 0.1 |
| Ascorbic acid | 0.1 |
| L-Arginine | 1.0 |
| Monoethanolamine | 8.0 |
| Salcare ® SC 96[44] | 0.1 |
| Perfume oil | 0.3 |
| p-Phenylenediamine dihydrochloride | 0.09 |
| p-Tolylenediamine sulfate | 0.11 |
| N,N-Bis(2'-hydroxyethyl)-p-phenylenediamino sulfate | 0.06 |
| 2-(2'-Hydroxyethyl)-p-phenylenediamine sulfate | 0.06 |
| 2,4-Bis(2'-hydroxyethyl)amino-6-methylanisole | 0.34 |
| 1-Phenyl-3-methylpyrazol-5-one | 0.05 |
| 6-Hydroxyindole | 0.1 |
| HC Red 1 | 0.1 |
| 4-Amino-3-nitrophenol | 0.05 |
| HC Red 54 | 0.05 |
| 1,4-Diamino-2-nitrobenzene | 0.05 |
| Acid Red 52[45] | 0.1 |
| Acid Red 33[46] | 0.1 |
| Water | ad 100 |

[42]Oleic acid (INCI name: Oleic Acid) (Cognis)
[43]$C_{12-14}$-fatty alcohol with about 2 EO units (INCI name: Laureth-2) (Cognis)
[44]about 50% active substance content; INCI name: Polyquaternium-37, Propylene Glycol Dicaprylate/Dicaprate, PPG-1 Trideceth-6 (CIBA)
[45]CI 45100
[46]CI 17200

Formulations 1 to 10 were mixed with the above-described oxidizing agent preparation (point 2.1) in the ratio 1:1, and the resulting application preparation was applied to tresses (Kerling, naturally white). After a contact time of 30 minutes at room temperature, the fibers were thoroughly rinsed with water, dried with hair dryer and the colorations were assessed. The following results were obtained:

| Formulation number | Color result |
|---|---|
| 1 | intense wine red |
| 2 | intense violet |
| 3 | intense orange-red |
| 4 | blackish red |

-continued

| Formulation number | Color result |
| --- | --- |
| 5 | dark violet |
| 6 | dark ruby |
| 7 | dark aubergine |
| 8 | strawberry red |
| 9 | luminous orange-red |
| 10 | luminous red |

What is claimed is:

1. A composition comprising 2,4-Bis[(2-hydroxyethyl) amino]-6-methylanisole in a weakly alkaline medium.

2. A composition comprising 2,4-bis[(3-hydroxypropyl) amino]-6-methylanisole in a weakly alkaline medium.

3. The composition of claim 1 further comprising p-tolylenediamine.

4. The composition of claim 1 further comprising 1-(2-hydroxyethyl)-2,5-diaminobenzene.

5. The composition of claim 1 further comprising bis(2-hydroxy-5-aminophenol)methane.

6. The composition of claim 1 further comprising 2,4,5,6-tetraaminopyrimidine.

7. The composition of claim 1, further including a direct dye.

8. The composition of claim 7, wherein the direct dye is a cationic direct dye.

9. The composition of claim 2, further including a direct dye.

10. The composition of claim 9, wherein the direct dye is a cationic direct dye.

11. An agent for coloring keratin fibers, in particular, human hair, comprising, in a cosmetic acceptable carrier, as coupler component, at least one m-phenylenediamine derivative selected from the group consisting of 2,4-bis[(2-hydroxyethyl)amino]-6-methylanisole and 2,4-bis[(3-hydroxypropyl)amino]-6-methyl anisole and having a pH of 9–12.

12. The agent of claim 11, wherein the coupler component is 2,4-bis[(2-hydroxyethyl)amino]-6-methylanisole.

13. The agent as claimed in claim 12, further comprising p-tolylenediamine.

14. The agent as claimed in claim 12, further comprising 1-(2-hydroxyethyl)-2,5-diaminobenzene.

15. The agent as claimed in claim 12, further comprising bis(2-hydroxy-5-aminophenol)methane.

16. The agent as claimed in claim 12, further comprising 2,4,5,6-tetraaminopyrimidine.

17. The agent as claimed in claim 11, further including a direct dye.

18. The agent as claimed in claim 17, wherein the direct dye is a cationic direct dye.

19. A method of coloring keratin fibers in which an agent as claimed in claim 11 is applied to the fibers and is rinsed off again after a contact time.

20. A method of coloring keratin fibers in which an agent as claimed in claim 17 is applied to the fibers and is rinsed off again after a contact time.

* * * * *